United States Patent [19]
Vora

[11] 4,024,200
[45] May 17, 1977

[54] COUNTERCURRENT FLOW REACTION CHAMBER FOR PLURAL STAGES OF HF ALKYLATION

[75] Inventor: Bipin V. Vora, Wheeling, Ill.

[73] Assignee: UOP Inc., Des Plaines, Ill.

[22] Filed: May 5, 1976

[21] Appl. No.: 683,354

Related U.S. Application Data
[62] Division of Ser. No. 533,422, Dec. 16, 1974, abandoned.

[52] U.S. Cl. .................. 260/671 R; 260/683.45; 260/683.48
[51] Int. Cl.² .................................. C07C 3/54
[58] Field of Search ...... 260/683.48, 671 R, 666 P, 260/683.43, 683.58, 683.45

[56] References Cited
UNITED STATES PATENTS

| | | | |
|---|---|---|---|
| 2,365,426 | 12/1944 | Molique | 260/683.58 |
| 3,435,092 | 3/1969 | Hutson, Jr. et al. | 260/683.43 |
| 3,707,580 | 12/1972 | Anderson | 260/683.48 |
| 3,914,111 | 10/1975 | Anderson | 260/683.48 |
| 3,966,417 | 6/1976 | Chapman | 260/683.48 |

Primary Examiner—George Crasanakis
Attorney, Agent, or Firm—James R. Hoatson, Jr.; Robert W. Welch; William H. Page, II

[57] ABSTRACT

An alkylatable reactant is alkylated with an olefin-acting reactant, utilizing a fluid HF catalyst in a countercurrent flow reaction chamber wherein reactants are flowing upward and the fluid catalyst is flowing downward. The fluid catalyst enters the reaction chamber at the top and is withdrawn at the bottom. Reaction chamber effluent passes into a settling chamber wherein it is separated into a catalyst phase and a hydrocarbon phase, the latter passing through a second reaction chamber in which it contacts a countercurrent flow of higher concentration fluid HF catalyst, and into a final settling chamber, wherein a hydrocarbon reaction product phase is separated from a catalyst phase and withdrawn. Also disclosed is a novel unitary alkylation vessel comprising, in combination, a countercurrent reaction chamber, a settling chamber, a second reaction chamber, and a final settling chamber.

8 Claims, 2 Drawing Figures

COUNTERCURRENT FLOW REACTION CHAMBER FOR PLURAL STAGES OF HF ALKYLATION

CROSS-REFERENCE TO RELATED APPLICATIONS

This application is a division of application Ser. No. 533,422, filed Dec. 16, 1974, now abandoned.

BACKGROUND OF THE INVENTION

This invention relates to a process for producing an alkylation reaction product from an alkylatable reactant and an olefin-acting reactant utilizing a fluid catalyst.

This invention also relates to a novel unitary vessel for producing an alkylation reaction product.

In one aspect, this invention relates to a process and apparatus, utilizing a fluid catalyst, for producing an isoparaffin-olefin reaction product which may be used as a motor fuel component. This process and apparatus herein disclosed provide a method for producing an isoparaffin olefin reaction product which possesses excellent anti-knock properties and which may be utilized to upgrade the octane level of unleaded motor fuels.

Alkylation processes are employed to create higher molecular weight compounds from lower molecular weight olefin-acting compounds and alkylatable compounds. For example, aromatic hydrocarbons may be alkylated with $C_{10}$–$C_{20}$ olefins to produce higher molecular weight alkylaromatics which are useful as detergents. Aromatics may also be alkylated with $C_2$–$C_{10}$ olefins to produce resin and plastics precursors such as ethylbenzenes, propylbenzenes, etc.

Among the most important products of fluid-catalyzed alkylation is the motor fuel alkylate produced in acid-catalyzed alkylation of $C_4$—$C_6$ isoparaffins with $C_3$—$C_5$ olefins. Generally, isobutane is alkylated with butene isomers or mixture of propene and butenes utilizing hydrogen fluoride or sulfuric acid as a catalyst. The alkylate made in these processes generally has a fairly high octane rating which may be improved significantly by the addition of alkyl lead compounds. When such compounds as tetramethyl or tetraethyl lead are added to this alkylate product, its octane rating is high enough that it may be blended with other hydrocarbon components to create a motor fuel product having a desirably high octane rating. At present, it has been found desirable to minimize the use of alkyl lead compounds to upgrade the octane rating of motor fuel alkylate. At the same time, motor fuel octane requirements remain high. There is thus, a present demand for motor fuel alkylate having a high enough octane rating without the addition of lead, or with very little lead, that it may be used economically as a motor fuel blending component. The alkylation processes and apparatus which are presently in use do not produce a product of sufficiently high octane to meet this demand in an economical manner. The process and apparatus herein disclosed provide a method for producing a higher octane alkylate needed to satisfy the demand for high octane unleaded motor fuels.

One of the problems associated with hydrogen halide-catalyzed alkylation processes, particularly those employing a hydrogen fluoride catalyst, has been the production of alkyl halides, which are undesirable in the final products of alkylation processes, but are troublesome to separate from more valuable reaction products. For example, in an isoparaffine-olefin alkylation process employing hydrogen fluoride catalyst, the reactants and catalyst are thoroughly mixed to form a reaction mixture. After the alkylation reaction has taken place, the product and unconsumed reactants form one phase and the catalyst forms a second phase. The alkyl halides created collect in the reaction products phase. Since these halides can be reacted with alkylatable reactant in the presence of high purity acid catalyst to form the desired products, it is desirable to eliminate them in this way, rather than by attempting to separate them from desirable products.

SUMMARY OF THE INVENTION

Therefore, it is an object of this invention to provide a process for producing an alkylation reaction product from an alkylatable reactant and an olefin-acting reactant.

Another object of this invention is to provide a process for alkylating the alkyl halides formed in an alkylation reaction.

Still another object of this invention is to provide a novel apparatus for producing an alkylation reaction product utilizing a fluid catalyst.

The present invention embodies a process for producing an alkylation reaction product from an alkylatable reactant and an olefinacting reactant utilizing a hydrogen fluoride catalyst which comprises: (a) introducing a first catalyst-containing stream into an upper part of a vertically extended first reaction chamber maintained at alkylation reaction conditions, passing at least a portion of said catalyst-containing stream downwardly through said first reaction chamber and withdrawing the same from a bottom part of said first reaction chamber; (b) introducting said reactants into an intermediate part of said first reaction chamber and passing said reactants upwardly through said first reaction chamber in contact with said descending catalyst-containing stream; (c) processing the reaction mixture upwardly from said first reaction chamber through a vertically extended first settling chamber in open communication therewith and maintained at settling conditions, settling an entrained catalyst phase from said reaction mixture and returning said catalyst phase downwardly through said reaction chamber in admixture with said first catalyst- containing stream; (d) processing the hydrocarbon phase upwardly from said first settling chamber through a vertically extended second reaction chamber in open communication therewith and maintained at alkylation reaction conditions; (e) introducing a second catalyst-containing stream into an upper part of said second reaction chamber, passing at least a portion of said second catalyst-containing stream downwardly through said second reaction chamber in contact with said ascending hydrocarbon phase, and withdrawing said second catalyst-containing stream from a bottom part of said second reaction chamber; (f) processing the reaction mixture upwardly from said second reaction chamber through a vertically extended second settling chamber in open communication therewith and maintained at settling conditions, settling an entrained catalyst phase from said reaction mixture in said second settling chamber and returning said catalyst phase downwardly through said second reaction chamber in admixture with said second catalyst-containing stream; (g) withdrawing the hydrocarbon phase from an upper part of said second settling chamber and recovering said alkylation reaction product therefrom.

This invention further embodies a novel unitary acid-alkylation vessel which comprises in combination: (a) a vertically disposed reaction chamber having a first inlet means for introducing reactants therein at an intermediate locus, second inlet means for introducing acid catalyst therein at a locus above the locus at which reactants are introduced, and first outlet means for withdrawing acid catalyst at a locus below the locus at which reactants are introduced; (b) a vertically extended first settling chamber connected to the upper end of said reaction chamber, said first settling chamber communicating throughout its cross-section area with said reaction chamber; (c) a vertically extended second reaction chamber connected to the upper end of said first settling chamber, said reaction chamber communicating throughout its cross-section area with said first settling chamber, and having third inlet means for introducing acid catalyst at an upper locus and second outlet means for withdrawing acid catalyst at a locus below said third inlet means; and, (d) a vertically extended second settling chamber connected to the upper end of said second reaction chamber, said second settling chamber communicating throughout its cross-section area with said reaction chamber and having third outlet means for withdrawing reaction products.

DESCRIPTION OF THE DRAWING

Referring to FIG. 1, a fluid catalyst-containing stream is introduced into a reaction chamber 1 of an alkylation vessel 2 through conduit 3 and flows downwardly through reaction chamber 1. A catalyst-containing stream is withdrawn at the bottom of reaction chamber 1 through conduit 4. Alkylatable reactant and olefinacting reactant enter reaction chamber 1 through conduit 5 and are charged upwardly into the downwardly flowing catalyst stream by way of fluid distribution means 6 and a plurality of small diameter nozzles 7 connected to fluid distribution means 6 within reaction chamber 1. The reactants flow upwardly between a plurality of horizontally disposed U-bend tubes 8, which terminate on each end of the tubes at tube sheet 9. A baffle 10 separates the channel head 11 connected to tube sheet 9 into coolant inlet and outlet zones, into which coolant enters through conduit 12 and is withdrawn through conduit 13. The reactants continue flowing upwardly through reaction chamber 1, which is provided with a plurality of vertically spaced horizontal pans 14, resulting in mixing of the reactants with the downwardly flowing catalyst. Reaction chamber effluent comprising reaction products, unreacted reactants, and entrained catalyst flows upward into a settling chamber 15, wherein reaction chamber effluent is separated into a reaction effluent hydrocarbon phase which continues flowing upward, entering the reaction chamber 16, and a catalyst phase which returns downwardly into the reaction chamber 10. Reaction chamber 16 is provided with a plurality of vertically spaced horizontal pans 17. A second catalyst-containing stream is introduced into an upper part of reaction chamber 16 through conduit 19, and flows generally downward, countercurrent to the vertical flow of the reaction effluent hydrocarbon phase, into the partially enclosed space under the lowest pan of chamber 16 provided by horizontal baffle 20 and weir 21, from which space at least a portion of the second catalyst-containing stream is withdrawn from reaction chamber 16 through conduit 22. The reaction effluent hydrocarbon phase flows upwardly through reaction chamber 16, entering the final settling chamber 18 as reaction chamber effluent including entrained catalyst. Reaction chamber effluent is separated in settling chamber 18 into entrained catalyst which returns downwardly into reaction chamber 16 and a reaction product phase which flows upwardly through chamber 18, and is withdrawn at the top through conduit 23.

Referring to FIG. 2, there is shown a sectional detailed view of reaction chamber 1, taken along the line 2—2 of FIG. 1, illustrating an embodiment of the reactants fluid distribution therein. Reactants enter reaction chamber 1 through conduit 5 and are charged upward countercurrent into the downwardly, vertically moving stream of catalyst through a plurality of small diameter passageways in nozzles 7 of fluid distribution means 6.

DETAILED DESCRIPTION

Figure 1:
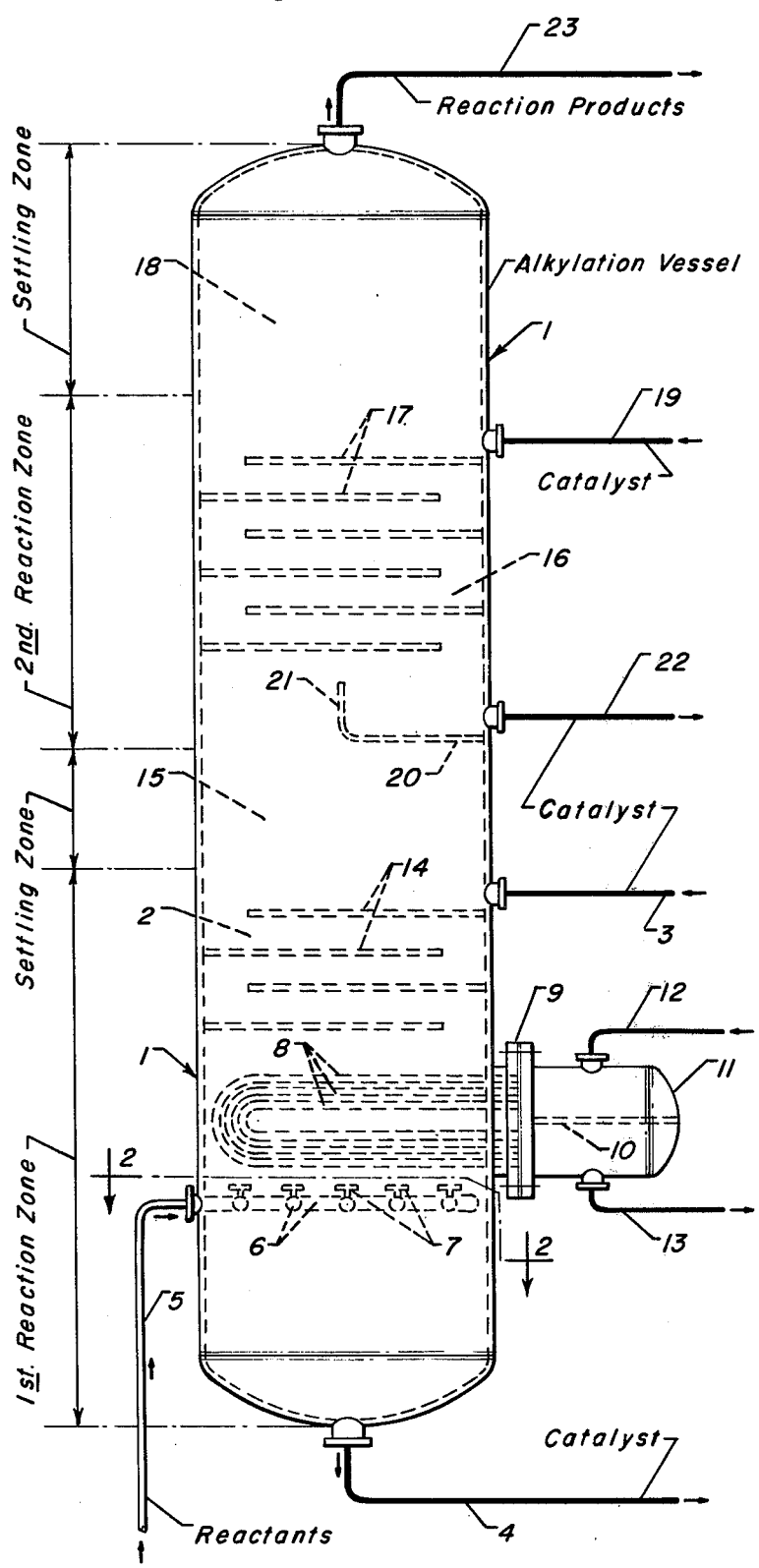
FIG. 1 is a vertically extended view of an embodiment of the alkylation apparatus of this invention.
Figure 2:
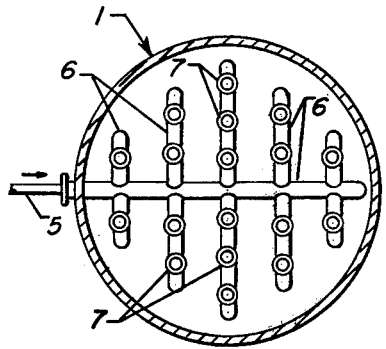
FIG. 2 is a section through the reaction chamber 1 of the vessel 2 of this invention shown in FIG. 1.

The method provided by this invention may be utilized to carry out a variety of fluid-catalyzed alkylation reactions. Examples of the catalysts suitable for use in an embodiment of the process and apparatus of this invention include sulfuric acid, hydrogen halides, boron halides, Friedel-Crafts catalyst, e.g., aluninum chloride, phosphoric acid, etc. Particularly suitable for use in an embodiment of the invention is a catalyst comprising from about 70 to about 100% hydrogen fluoride, by weight, and having, by weight, less than about 5% water content, and less than about 30% of other material including reactants, reaction products, etc. In an embodiment of this invention utilizing such a hydrogen fluoride catalyst, it is preferred that the portion of hydrogen fluoride catalyst charged to the reaction chamber comprise more than about 75% hydrogen fluoride, less than about 2% water and less than about 20%, by weight, of such materials as organic diluent, alkylatable reactant, etc. It is also preferred that the portion of catalyst introduced into the second reaction chamber of the apparatus of this invention comprises more than about 90% hydrogen fluoride, less than about 2% water and less than about 8% organic diluent, alkylatable reactant, etc.

Alkylatable reactants suitable for use in an embodiment of this invention include alkylatable aromatic hydrocarbons and alkylatable aliphatic hydrocarbons. Among the suitable aromatic hydrocarbons are benzene, mono and polyalkyl benzenes, polycyclic aromatics, etc. Suitable aliphatic hydrocarbons include, for example, branched and linear paraffins. Particular alkylatable reactants may be more suitably utilized in combination with one particular catalyst than with another. For example, the hydrogen fluoride catalyst described above is particularly suitable for use with an alkylatable reactant comprising branched paraffins, particularly isoparaffins, while a phosphoric acid type catalyst may more suitably be employed when the alkylatable reactant is an aromatic hydrocarbon. Particularly preferred for use in an embodiment of this invention is an isoparaffin hydrocarbon, especially isobutane.

Olefin-acting reactants which may be employed include mono- and poly-olefinic hydrocarbons, alkyl halides, alkyl sulfates, alkyl phosphates, alcohols, etc., which may be utilized more appropriately with one particular catalyst than with another. For example, alkyl halides may appropriately be used in an embodiment wherein a hydrogen halide or boron halide catalyst is employed, while alkyl sulfates are more suitable for an embodiment employing sulfuric acid. In an embodiment of the present invention employing the hydrogen fluoride catalyst noted above, it is preferred to utilize propene, 1- and 2-butenes and isobutylene. These mono-olefins may be used when diluted with other hydrocarbons such as propane, butanes, etc. In particular, 2-butene is a preferred olefin-acting reactant.

Alkylation conditions in the reaction chamber of the apparatus of this invention will be determined primarily by temperature and pressure of the catalyst and reactants when they enter the chambers. It is contemplated that the temperature within the apparatus of this invention will be controlled by cooling the reactants and catalyst internally be heat exchange means although means for influencing the temperature may be employed for external cooling.

Typical alkylation reaction products which may be produced in the process and apparatus herein disclosed include alkylaromatics such as ethylbenzenes, propylbenzenes, etc., as well as higher molecular weight alkylaromatics having $C_{10}$—$C_{20}$ alkyl groups, useful as detergents. One of the important alkylation reaction products which can be produced by the methods herein disclosed is the above-described motor fuel alkylate, which is generally a mixture of branched chain heptanes and octanes. In a motor fuel alkylate, trimethylpentanes are considered higher quality, more desirable reaction products than dimethylhexanes or branched chain heptanes.

It is preferred that fluid distribution means be provided within the reaction chamber of the apparatus of this invention in order to introduce the reactants into the downwardly flowing catalyst stream with as uniform distribution as possible throughout the cross-section of the reaction chamber, and with a high degree of dispersion to facilitate the formation of desirable reaction products. The sort of fluid distribution means utilized in a particular embodiment is not essential to the concept of this invention. A plurality of conduits and nozzles may be utilized as shown in the attached figure. Another suitable fluid distribution means comprises a nozzle having a plurality of small-diameter passageways through which reactants are passed into the downwardly flowing catalyst.

Mixing means which may suitably be employed in the reaction chambers of the apparatus herein disclosed includes vertically spaced horizontal perforated baffles, vertically spaced horizontal valve trays, column packing, baffle sections, etc. A particular embodiment of the mixing and contacting means is not essential to the concept of the present invention.

PREFERRED EMBODIMENT

In the preferred embodiment of the process and apparatus of this invention, a hydrogen fluoride catalyst as described above, is utilized to facilitate the alkylation of isobutane with propene and butenes. The alkylation reaction in this embodiment is exothermic, but it is desirable to avoid overly high temperatures in the reaction chamber because too high temperatures result in a lower quality alkylation reaction product. For this reason, it is necessary to introduce the catalyst, the reactants, or both, into the first reaction chamber at a temperature low enough that the heat released by the reaction will not cause the temperature of the reaction mixture to rise above the desired level. As noted above, all, or a part of the heat released in the alkylation reaction may be withdrawn from the apparatus by employing heat exchange means in the chamber. When heat is withdrawn from the process by cooling the reactants, catalyst, etc., before charging them to the first reaction chamber, the pre-cooling may be practiced on the fresh reactants charged, or recycled or freshly charged catalyst, recycled hydrocarbons, or any combination of the above. It is preferred that the temperature of the hydrogen fluoride catalyst and of the reactants charged to the reaction chamber be held within the range of from about 30°F. to about 140°f.

A preferred embodiment of this invention includes cooling means in the reaction chamber above the reactants inlet distribution means for the purpose of controlling the temperature rise of the reactants in the reaction zone, and cooling means in the reaction chamber below the reactants inlet distribution means for the purpose of cooling the catalyst, which is withdrawn from the reaction chamber bottom and returned by pumping means to the reaction chamber top as catalyst recycle. It is preferred that the temperature of the reactants in the reaction chamber be held within the range of about 60° to 160° F.

The catalyst is introduced into the reaction chamber at a volumetric ratio of about 1 to 10 times the total flow rate of reactants introduced, at an upper locus above the uppermost pan of the mixing means provided, which in the preferred embodiment comprises side-to-side, vertically spaced, horizontal pans. Flow of the catalyst is generally downward, countercurrent to the flow of reactants. Below the mixing means, the flowing catalyst is cooled by cooling means comprising a stab-in type, U-tube exchanger, in which cooling water is the coolant. Temperature of the reactants and catalyst is controlled at about 60° to 160° F. Below the cooling means, the flow of catalyst continues downwardly, passing the locus at which reactants are introduced into the reaction chamber, and below this locus, catalyst is again cooled by cooling means similar to said cooling means hereinabove stated to a temperature of about 60° to 160° F., before the catalyst is withdrawn from the bottom of the reaction chamber.

Reactants are introduced into the first reaction chamber in a volumetric ratio of isobutane to olefins of about 2 to 20 and a temperature of about 60° to 160° F. Reactants are distributed uniformly throughout the cross-section of the reaction chamber and dispersed by a plurality of small nozzles in a direction countercurrent to the flow of catalyst. Reactants may be introduced into the reaction chamber by various other distribution means, and the direction of introduction may be other than countercurrent to the flow of catalyst. At the locus of introduction of reactants into the reaction chamber, reactants are finely dispersed into the downwardly flowing catalyst. The lighter hydrocarbon reactants flow upwardly while the heavier catalyst flows downwardly. The upward flowing reactants are cooled by cooling means hereinabove stated, and are intimately contacted with catalyst by mixing means hereinabove stated, before flowing upwardly into the settling chamber as reaction chamber effluent, including a portion of entrained catalyst.

In the settling chamber, a lighter reaction effluent hydrocarbon phase comprising primarily reaction products and unconsumed reactants separates from a heavier catalyst phase comprising primarily hydrogen fluoride catalyst. Separation conditions maintained in the settling chamber include a temperature and pressure sufficient to maintain the catalyst and reaction products in the liquid phase. Preferably this includes a temperature of about 0° F. to 150° F., and a pressure of about 1 to 40 atmospheres. The separated catalyst phase flows downwardly due to the gravity difference between catalyst and hydrocarbon phases, and returns into the reaction chamber. The lighter hydrocarbon phase continues to flow upwardly into the second reaction chamber.

In the second reaction chamber, the hydrocarbon phase flows upwardly through the convoluted passageway provided by the plurality of vertically spaced, horizontal side-by-side pans of the mixing means. Simultaneously, relatively high purity hydrogen fluoride is introduced as a catalyst refluxing stream into the upper, downstream end of the reaction chamber, and flows downwardly, countercurrent to the reaction products phase. By means of the vertically-spaced pans, the high strength catalyst and reaction products are brought into intimate contact at refluxing conditions including a temperature of about 0° to 150° F. and sufficient pressure to maintain the catalyst and hydrocarbon phase as liquids. This results in conversion of alkyl fluorides, present in the reaction products phase, into the desired alkylation reaction product, and in more complete conversion of any olefin-acting reactants present. The refluxing catalyst may be wholly or partially withdrawn from the bottom of the second reaction chamber, or allowed to return into the settling chamber to be combined with the catalyst utilized in the reaction chamber. The hydrocarbon phase and entrained catalyst flow upwardly as a second reaction chamber effluent into a second, upper settling chamber, wherein the entrained catalyst settles at settling conditions similar to those previously stated and returns downwardly into the second reaction chamber. The resulting reaction product phase is withdrawn from the top of the settling chamber and further processed to recover the desired alkylation reaction product.

Among the benefits obtained from the invention herein disclosed, the reaction, mixing and settling chambers are all included in a unitary vessel, and the major portion of catalyst inventory is maintained in a single vessel. The uniqueness of the invention however is the combination of the benefits above with a reaction chamber in which catalyst and reactant flows are countercurrent, thus producing an alkylate product of superior quality.

I claim as my invention:

1. A process for producing an alkylation reaction product from an alkylatable reactant selected from the hydrocarbon group consisting of aromatic, branched paraffin and linear paraffin; and an olefin-acting reactant utilizing a hydrogen fluoride catalyst which comprises:

a. introducing a first hydrogen fluoride stream into an intermediate part of a vertically-extended reaction chamber to pass said first stream downwardly through a first alkylation zone in the lower part of said reaction chamber maintained at first alkylation reaction conditions and withdrawing said first alkylate stream from the bottom part of said reaction chamber;

b. introducing said alkylatable and said olefin-acting reactants into the lower part of said first alkylation zone and passing said reactants upwardly through said reaction chamber in contact with said descending first hydrogen fluoride stream to form a first alkylate reaction mixture;

c. passing said reaction mixture from step (b) upwardly in said reaction chamber through a first settling zone maintained at settling conditions to settle a hydrocarbon phase from an entrained catalyst phase in said first reaction mixture and passing said catalyst phase downwardly through said first alkylation zone in admixture with said first hydrogen fluoride stream;

d. passing said hydrocarbon phase upwardly from said first settling zone through a second alkylation zone in the upper part of said reaction chamber maintained at second alkylation reaction conditions;

e. introducing a second hydrogen fluoride stream into said upper part of said reaction chamber to pass said second hydrogen fluoride stream downwardly through said second alkylation reaction zone in contact with said ascending hydrocarbon phase to form a second alkylate reaction mixture and withdrawing said second hydrogen fluoride stream from the lower part of said second alkylation reaction zone;

f. passing said reaction mixture from step (e) upwardly from said second alkylation zone through a second settling zone to settle a hydrocarbon phase from an entrained catalyst phase in said second reaction mixture and passing said catalyst phase downwardly through said second alkylation zone in admixture with said second hydrogen fluoride stream, and g. withdrawing the hydrocarbon phase from said second settling zone and recovering said alkylation reaction product therefrom.

2. The process of claim 1 further characterized in that said second hydrogen fluoride stream contains a higher concentration of hydrogen fluoride than said first catalyst-containing stream.

3. The process of claim 1 further characterized with respect to step (a) in that said hydrogen fluoride stream comprises at least about 75 wt. % hydrogen fluoride, and with respect to step (e) in that said catalyst-containing stream comprises at least about 90 wt. % hydrogen fluoride.

4. The process of claim 1 further characterized with respect to step (a) in that at least a portion of hydrogen fluoride stream withdrawn from a bottom part of said first reaction chamber is recycled to the upper part of said first alkylation zone as a portion of said first hydrogen fluoride stream introduced in step (a).

5. The process of claim 1 further characterized with respect to step (e) in that at least a portion of said hydrogen fluoride stream withdrawn from the lower part of said second alkylation zone is recycled to the upper part of said second reaction chamber as a portion of said second hydrogen fluoride stream introduced in step (e)

6. The process of claim 1 further characterized in that said alkylatable reactant is an isoparaffin having 4 to 6 carbon atoms per molecule and said olefin-acting reactant is an olefin having from 3 to 5 carbon atoms per molecule.

7. The process of claim 1 further characterized in that said alkylatable reactant is isobutane and said olefin acting reactant is a butene-propene mixture.

8. The process of claim 1 further characterized with respect to step (a) in that said alkylation reaction conditions include a temperature of from about 60° to about 160° F., and with respect to step (d) in that said alkylation reaction conditions include a temperature of from about 0° to about 150° F.

* * * * *